US008529504B2

(12) United States Patent
Gibson et al.

(10) Patent No.: US 8,529,504 B2
(45) Date of Patent: Sep. 10, 2013

(54) ARTICULATED CATHETER

(75) Inventors: Charles A. Gibson, Malden, MA (US);
Gary O'Boyle, North Andover, MA
(US); Gary S. Falwell, Moultonborough,
NH (US)

(73) Assignee: C.R. Bard, Inc., Murray Hill, NJ (US)

( * ) Notice: Subject to any disclaimer, the term of this patent is extended or adjusted under 35 U.S.C. 154(b) by 3 days.

(21) Appl. No.: 13/185,488

(22) Filed: Jul. 18, 2011

(65) Prior Publication Data

US 2011/0270173 A1 Nov. 3, 2011

Related U.S. Application Data

(63) Continuation of application No. 10/536,109, filed as application No. PCT/US2005/017338 on May 17, 2005, now Pat. No. 8,007,462.

(60) Provisional application No. 60/571,732, filed on May 17, 2004.

(51) Int. Cl.
*A61M 31/00* (2006.01)
*A61M 37/00* (2006.01)
*A61M 25/00* (2006.01)

(52) U.S. Cl.
USPC ............... 604/95.04; 604/525; 604/95.01

(58) Field of Classification Search
USPC .................................. 604/95.01, 95.04, 525
See application file for complete search history.

(56) References Cited

U.S. PATENT DOCUMENTS

| | | |
|---|---|---|
| 4,430,083 A | 2/1984 | Ganz et al. |
| 4,920,980 A | 5/1990 | Jackowski |
| 4,934,340 A | 6/1990 | Ebling et al. |
| 5,125,896 A | 6/1992 | Hojeibane |
| 5,167,647 A | 12/1992 | Wijkamp et al. |
| 5,242,441 A | 9/1993 | Avitall |
| 5,269,757 A | 12/1993 | Fagan et al. |
| RE34,502 E | 1/1994 | Webster, Jr. |
| 5,318,525 A | 6/1994 | West et al. |
| 5,364,352 A | 11/1994 | Cimino et al. |
| 5,368,564 A | 11/1994 | Savage |
| 5,383,852 A | 1/1995 | Stevens-Wright |

(Continued)

FOREIGN PATENT DOCUMENTS

| | | |
|---|---|---|
| WO | WO 93/20878 | 10/1993 |
| WO | WO 01/72234 | 10/2001 |

OTHER PUBLICATIONS

Chugh et al.; "Catheter Tip Orientation Affects Radiofrequency Ablation Lesion Size in the Canine Left Ventricle"; Pace, vol. 22, pp. 413-420.

(Continued)

*Primary Examiner* — Nicholas Lucchesi
*Assistant Examiner* — Rebecca E Eisenberg
(74) *Attorney, Agent, or Firm* — Wolf, Greenfield & Sacks, P.C.

(57) ABSTRACT

Methods and apparatuses for manipulating an elongated flexible shaft of a catheter provide ease and reliability of positioning electrodes against or near tissue. Dual-bend flexible distal tips may be used in combination with flat wires. In some embodiments, flat wires which are free to rotate upon initial bending of shaft segments are employed. In some embodiments, one or more transition segments are used to relocate the satellite lumen-to-main lumen transition of pull wires away from a change in shaft stiffness.

20 Claims, 5 Drawing Sheets

(56) References Cited

U.S. PATENT DOCUMENTS

| | | |
|---|---|---|
| 5,445,148 A | 8/1995 | Jaraczewski et al. |
| 5,462,527 A | 10/1995 | Stevens-Wright et al. |
| 5,482,037 A | 1/1996 | Borghi |
| 5,487,757 A | 1/1996 | Truckai et al. |
| 5,489,270 A | 2/1996 | van Erp |
| 5,545,200 A | 8/1996 | West et al. |
| 5,562,619 A | 10/1996 | Mirarchi et al. |
| 5,582,609 A | 12/1996 | Swanson et al. |
| 5,609,151 A | 3/1997 | Mulier et al. |
| 5,611,777 A | 3/1997 | Bowden et al. |
| 5,626,130 A | 5/1997 | Vincent et al. |
| 5,642,736 A | 7/1997 | Avitall |
| 5,643,231 A | 7/1997 | Lurie et al. |
| 5,656,029 A | 8/1997 | Imran et al. |
| 5,673,695 A | 10/1997 | McGee et al. |
| 5,680,860 A | 10/1997 | Imran |
| 5,690,617 A | 11/1997 | Wright |
| 5,715,817 A | 2/1998 | Stevens-Wright et al. |
| 5,720,300 A | 2/1998 | Fagan et al. |
| 5,755,760 A | 5/1998 | Maguire et al. |
| 5,779,669 A | 7/1998 | Haissaguerre et al. |
| 5,782,760 A | 7/1998 | Schaer |
| 5,782,828 A | 7/1998 | Chen et al. |
| 5,807,249 A | 9/1998 | Qin et al. |
| 5,820,591 A | 10/1998 | Thompson et al. |
| 5,823,955 A | 10/1998 | Kuck et al. |
| 5,826,576 A | 10/1998 | West |
| 5,827,272 A | 10/1998 | Breining et al. |
| 5,843,152 A | 12/1998 | Tu et al. |
| 5,865,800 A | 2/1999 | Mirarchi et al. |
| 5,893,884 A | 4/1999 | Tu |
| 5,906,590 A | 5/1999 | Hunjan et al. |
| 5,916,214 A | 6/1999 | Cosio et al. |
| 5,931,811 A | 8/1999 | Haissaguerre et al. |
| 5,935,102 A | 8/1999 | Bowden et al. |
| 5,938,603 A | 8/1999 | Ponzi |
| 5,938,694 A | 8/1999 | Jaraczewski et al. |
| 5,984,909 A | 11/1999 | Lurie et al. |
| 5,987,344 A | 11/1999 | West |
| 6,001,085 A | 12/1999 | Lurie et al. |
| 6,002,955 A | 12/1999 | Willems et al. |
| 6,006,125 A | 12/1999 | Kelly et al. |
| 6,035,224 A | 3/2000 | West |
| 6,064,902 A | 5/2000 | Haissaguerre et al. |
| 6,066,125 A * | 5/2000 | Webster, Jr. .......... 604/528 |
| 6,074,368 A | 6/2000 | Wright |
| 6,083,222 A | 7/2000 | Klein et al. |
| 6,123,699 A | 9/2000 | Webster, Jr. |
| 6,146,379 A | 11/2000 | Fleischman et al. |
| 6,156,027 A | 12/2000 | West |
| 6,156,034 A | 12/2000 | Cosin et al. |
| 6,169,916 B1 | 1/2001 | West |
| 6,173,699 B1 | 1/2001 | Kasen |
| 6,196,916 B1 | 3/2001 | Childs |
| 6,198,974 B1 | 3/2001 | Webster, Jr. |
| 6,224,587 B1 | 5/2001 | Gibson |
| 6,236,224 B1 | 5/2001 | Schneider |
| 6,263,224 B1 | 7/2001 | West |
| 6,319,250 B1 | 11/2001 | Falwell et al. |
| 6,551,271 B2 | 4/2003 | Nguyen |
| 6,571,131 B1 | 5/2003 | Nguyen |
| 6,572,611 B1 | 6/2003 | Falwell |
| 6,638,278 B2 | 10/2003 | Falwell et al. |
| 6,976,987 B2 | 12/2005 | Flores |
| 2002/0072663 A1 | 6/2002 | Fuimaono et al. |
| 2003/0130712 A1 | 7/2003 | Smits et al. |
| 2004/0147827 A1 | 7/2004 | Bowe |

OTHER PUBLICATIONS

International Search Report and Written Opinion for International Application No. PCT/US2005/017338.
http://www.medtronic.com/epsystems/ablation_catheters.html printed on Nov. 14, 2006 (9 pages).
News Release dated Jan. 31, 2002, http://wwwp.medtronic.com/Newsroom printed on Nov. 14, 2006 (2 pages).

* cited by examiner

ARTICULATED CATHETER

RELATED APPLICATIONS

This application is a continuation under 35 U.S.C. §120 of U.S. application Ser. No. 10/536,109, filed on Jan. 22, 2008, which is herein incorporated by reference in its entirety, and which is a national stage filing of International Application No. PCT/US2005/017338, filed May 17, 2005, which claims priority under 35 U.S.C. §119(e) to U.S. Provisional Application Ser. No. 60/571,732 entitled "ARTICULATED CATHETER" and filed on May 17, 2004, which is herein incorporated by reference in its entirety.

BACKGROUND OF INVENTION

1. Field of Invention

The invention relates generally to mapping and/or ablation catheters, and more specifically to methods and apparatuses for manipulating elongated, flexible shafts.

2. Discussion of Related Art

The human heart is a very complex organ which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

In some individuals, the electrical impulses of the heart develop an irregular propagation, disrupting the heart's normal pumping action. The abnormal heartbeat rhythm is termed a "cardiac arrhythmia." Arrhythmias may occur when a site other than the sinoatrial node of the heart is initiating rhythms (i.e., a focal arrhythmia), or when electrical signals of the heart circulate repetitively in a closed circuit (i.e., a reentrant arrhythmia).

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions. When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

SUMMARY OF INVENTION

According to one embodiment of the invention, a catheter comprises an elongated flexible shaft including a flexible distal tip having a first segment that is bendable, a second segment that is immediately proximal to the first segment and has a stiffness that is greater than the first segment, a main shaft that is proximal to the flexible distal tip, a pull wire main lumen, and a first pull wire satellite lumen, the first pull wire satellite lumen extending from the first bendable segment into the second segment. The catheter further comprises a first pull wire that has a distal portion anchored within the flexible distal tip, travels within the first pull wire satellite lumen and into the pull wire main lumen, and attaches to a first pull wire actuation element.

In some embodiments, the first pull wire satellite lumen may extend at least two millimeters into the second segment, at least three millimeters into the second segment, at least five millimeters into the second segment, at least ten millimeters into the second segment, or through the entire length of the second segment. The second segment may be formed of the same materials as the main shaft. The second segment may be separately distinguishable from the main shaft. In some embodiments the second segment is less stiff than the main shaft, while in other embodiments, the second segment is stiffer than the main shaft.

In some embodiments, the catheter further comprises a second pull wire satellite lumen that extends from the first bendable segment into the second segment, and a second pull wire that is anchored within the flexible distal tip, travels within the second pull wire satellite lumen and into the pull wire main lumen, and attaches to a second pull wire actuation element. Actuating the second pull wire actuation element bends the first bendable segment in a direction that is different from a direction that the first bendable segment bends in response to actuation of the first pull wire actuation element.

In some embodiments, the first bendable segment is a distal bending segment and the flexible distal tip further comprises a proximal bending segment, the first pull wire being anchored within one of the proximal bending segment and the distal bending segment, and a third pull wire being anchored within the other of the proximal bending segment and the distal bending segment, the third pull wire being attached to a third pull wire actuation element.

In some embodiments, actuation of the first pull wire actuation element bends one of the proximal bending segment and the distal bending segment in a direction opposite to the direction that the other of the proximal bending segment and the distal bending segment bends in response to actuation of the third pull wire actuation element.

In some embodiments, the first pull wire is anchored within the distal bending segment, the third pull wire is anchored within the proximal bending segment, and actuation of the first pull wire actuation element and the third pull wire actuation element bends the distal bending segment and the proximal bending segment within substantially the same plane. In some embodiments, actuation of the first pull wire actuation element bends the distal bending segment in a direction opposite to the direction that the proximal bending segment bends in response to actuation of the third pull wire actuation element.

In some embodiments, the catheter further comprises a second pull wire satellite lumen, and a second pull wire that has a distal portion anchored within the distal bending segment of the flexible distal tip, travels within the second pull wire satellite lumen and into the pull wire main lumen, and attaches to a second pull wire actuation element. The catheter further comprises a fourth pull wire satellite lumen, and a fourth pull wire that has a distal portion anchored within the proximal bending segment of the flexible distal tip, travels within the fourth pull wire satellite lumen and into the pull wire main lumen, and attaches to a fourth pull wire actuation element. Actuation of the second pull wire actuation element bends the distal bending segment of the flexible distal tip in a direction that is different from a direction that the distal bending segment bends in response to actuation of the first pull wire actuation element. Actuation of the fourth pull wire actuation element bends the proximal bending segment of the flexible distal tip in a direction that is different from a direction that the proximal bending segment bends in response to actuation of the third pull wire actuation element.

In some embodiments, the catheter further comprises a flat wire and a flat wire lumen, the flat wire extending along at least a portion of the flexible distal tip within the flat wire lumen. The flat wire has a distal end and a proximal end, and the distal end may not be secured. The flat wire has a distal end and a proximal end, and the distal end may be free to rotate upon initial bending of the flexible distal tip.

According to another embodiment of the invention, a catheter comprises an elongated flexible shaft comprising a pull wire lumen, a pull wire for bending a first segment of the elongated flexible shaft, the pull wire being anchored within the elongated flexible shaft, extending through the pull wire lumen and attachable to a pull wire actuation element. The catheter further comprises a flat wire lumen and a flat wire positioned within the flat wire lumen and having a longitudinal axis, a proximal end and a distal end, the flat wire being free to rotate about the longitudinal axis upon initial bending of the first segment.

The flat wire lumen and the flat wire may be constructed and arranged such that upon further bending of the first segment, contact between the flat wire and the flat wire lumen prevents the flat wire from rotating. The catheter may further comprise a second segment that is a proximal bending segment of a flexible distal tip, wherein the first segment is a distal segment of the flexible distal tip. The flat wire may maintain the first and second segments in substantially the same plane when at least one of the segments is bent. The first and second segments may be bendable in opposite directions. The first and second segments may be independently bendable. In some embodiments, the first segment may be bendable in a first plane and the second segment may be independently bendable in a different plane.

According to a further embodiment of the invention, a catheter comprises an elongated flexible shaft comprising a main shaft portion, a first pull wire disposed within the elongated flexible shaft, a second pull wire disposed within the elongated flexible shaft, and a flexible distal tip including a proximal bending segment and a distal bending segment, the proximal bending segment being bendable by pulling the first pull wire such that the proximal bending segment bends in a first direction and within a plane, the distal bending segment being bendable by pulling the second pull wire such that the distal bending segment bends in a second direction that is opposite to the first direction and substantially within the same plane as the proximal bending segment. The catheter further comprises a flat wire lumen and a flat wire extending through the flat wire lumen.

In some embodiments, the flat wire maintains the proximal and distal bending segments in substantially the same plane when at least one of the segments is bent. The proximal and distal bending segments may be bendable in opposite directions. In some embodiments, the proximal and distal bending segments are independently bendable.

In some embodiments, the catheter further comprises a transition segment interposed between the distal bending segment and the proximal bending segment, the transition segment having a stiffness that is greater than the distal bending segment. The catheter further comprises a pull wire main lumen and a pull wire satellite lumen for guiding the second pull wire, the pull wire satellite lumen extending from the distal bending segment into and through the transition segment, wherein the second pull wire is guided into the pull wire main lumen at a location that is proximal to the transition segment.

According to further embodiments, methods of using catheters described herein comprise the steps of introducing a catheter into a patient, and actuating pull wires of the catheter to manipulate a flexible distal tip into configurations described herein using one or more of the elongated flexible shaft embodiments described herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The catheters described herein may be used to perform electrophysiology procedures at a region of the heart sought to be diagnosed or treated. In particular, the distal bending segment of a catheter may be positioned at a desired location in the heart such that one or more ablation, pacing, and/or mapping electrodes located on the distal bending segment are in contact with the heart.

System Overview

Figure 1:
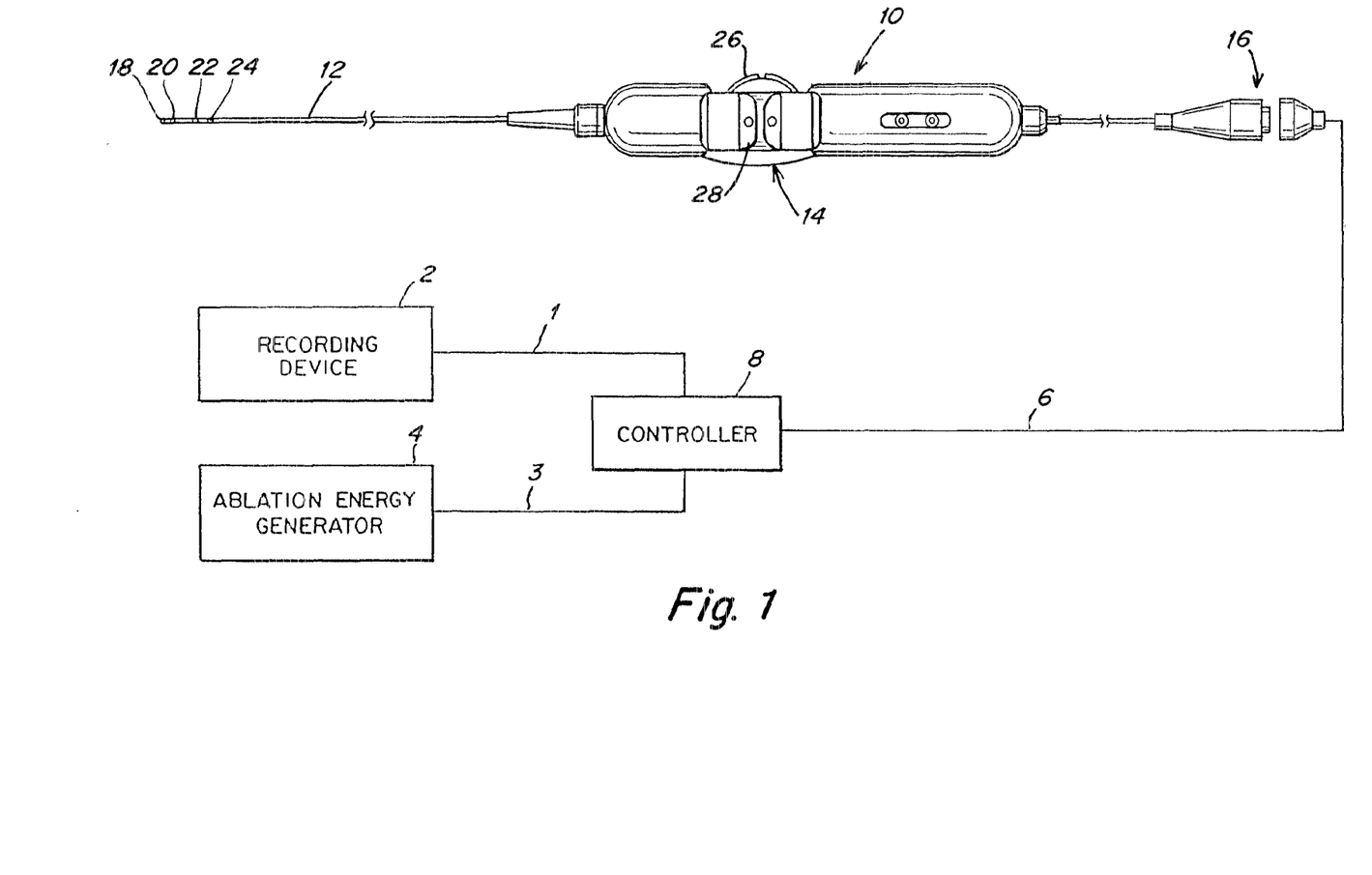
FIG. 1 illustrates an overview of a mapping and/or ablation catheter system in accordance with one embodiment of the present invention.

Reference is now made to FIG. 1, which illustrates an overview of a mapping and/or ablation catheter system in accordance with one embodiment of the present invention. The system includes a catheter 10 having a shaft portion 12, a control handle 14, a connector portion 16, and electrodes 18, 20, 22 and 24. Control handle 14 may include actuation elements, such as a thumb wheel 26 or a slider 28, for bending segments of shaft portion 12. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided to catheter 10 by ablation energy generator 4. When used in a mapping application, controller 8 is used to process signals coming from catheter 10 and to provide these signals to recording device 2. Although illustrated as separate devices, recording device 2, ablation energy generator 4, and controller 8 could be incorporated into a single device or two devices.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping and/or ablation procedures.

Figures 2A, 2B:
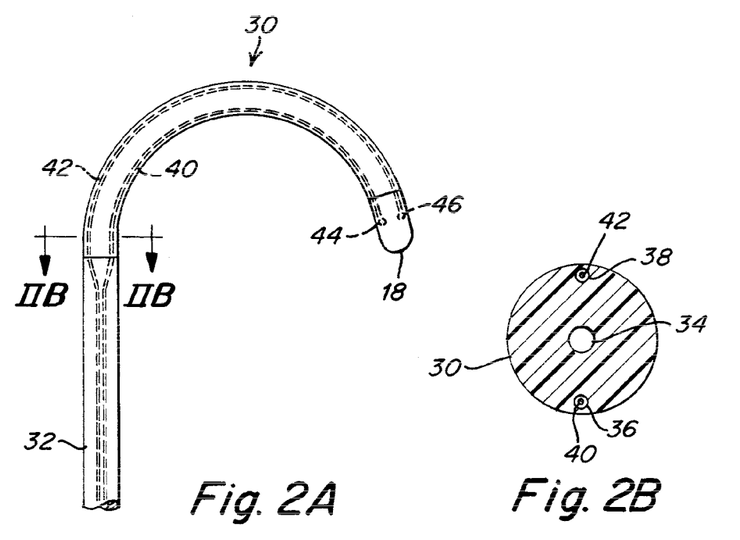
FIG. 2A illustrates a conventional embodiment of a pull wire arrangement in a catheter having a flexible distal tip.
FIG. 2B is a cross-sectional view taken along line IIB-IIB of FIG. 2A.

FIGS. 2A and 2B show a conventional catheter having a flexible distal tip 30, a main shaft 32, a distal tip electrode 18, a lumen 34 for electrode lead wires, first and second pull wire satellite lumens 36 and 38, and first and second pull wires 40 and 42. Distal ends of pull wires 40 and 42 are anchored at anchor locations 44 and 46, respectively, within the flexible tip. Proximal ends of pull wires 40, 42 are anchored to pull wire actuation elements (not shown). Pull wires 40, 42 travel through pull wire satellite lumens 36, 38 in the flexible distal tip and then transition to a pull wire main lumen at the transition of flexible distal tip 30 to main shaft 32. A pull wire main lumen is not shown in FIGS. 2A and 2B, but a pull wire main lumen 54 is shown in FIG. 3C.

Flexible distal tip 30 has a lower stiffness than main shaft 32. As such, when first pull wire 40 is pulled, flexible distal tip 30 bends in a first direction (to the right as viewed in FIG. 2A), with the bend starting approximately at the transition of flexible distal tip 30 to main shaft 32. The difference in stiffness of main shaft 32 and flexible distal tip 30 can be accomplished in various ways, including using different shaft materials and/or including stiffener wires within the elongated shaft. A desired location and configuration of a bend may be achieved by selecting the anchor location of the pull wires and the stiffnesses of various segments of the elongated flexible shaft.

It should be noted that for purposes herein, the term "stiffness" refers to bending stiffness. The stiffness of a shaft, a distal tip, or a bending segment is not intended to be restricted to the stiffness of shaft material, but rather to the bending stiffness of the element as a whole (for example, a shaft may include stiffening wires) in the relevant bending direction.

The term "pull wire satellite lumen", for purposes herein, refers to a lumen through which a pull wire can be passed, the satellite lumen being positioned at a radial distance from a center axis of the elongated flexible shaft, or a reference axis in the case of a shaft that does not have a center axis. A pull wire main lumen is typically positioned near to or on a center axis of the elongated flexible shaft, although such a position is not required.

Lumens given certain names in the present application are not restricted in use to their given names. For instance, a pull wire lumen may include an electrode wire or a stiffening wire in addition to a pull wire, and thereby also function as an electrode wire lumen.

The pull wire actuation elements mentioned above may include a thumb wheel or a slider, as described with reference to FIG. 1. The term "pull wire actuation element" can refer to the connection location of the pull wire to the thumb wheel (or slider, or other element), such that a single thumb wheel may have two (or more) actuation elements—one each for the pull wires that are connected to the thumb wheel. In some embodiments, two pull wires that bend a catheter segment in opposite directions are attached to the same thumb wheel or slider. The term "pull wire actuation element" can also refer to the thumb wheel (or slider or other element) as a whole. The type or types of pull wire actuation elements used are not intended to be limiting.

Transition Segment

A transition segment is included in certain embodiments of the catheter to improve the reliability and/or ease of distal tip manipulation. As shown in FIG. 3B, a transition segment 48, having a higher stiffness than flexible distal tip 30, includes satellite lumens 50 and 52 such that pull wires 40, 42 are positioned toward the outer radial edge of the catheter proximal to the start of the bend of flexible distal tip 30. In the conventional catheter shown in FIG. 2A, the transition of the pull wires from the satellite lumens to the main lumen occurs at approximately the same location as the transition from the flexible distal tip to the main shaft, the distal tip to main shaft transition representing a change in stiffness. According to embodiments of the invention, the transition of the pull wires occurs proximal to the change in stiffness.

Transition segment 48 may have the same stiffness as main shaft 32, or it may have a stiffness that is in between the stiffness of main shaft 32 and the stiffness of flexible distal tip 30. In some embodiments, transition segment 48 is part of main shaft 32, i.e., the transition of the pull wires from the satellite lumens to the main lumen occurs within the main shaft at a certain distance proximal to the distal end of main shaft 32.

As shown in FIG. 3B, within transition segment 48, satellite lumens 50, 52 may be positioned from a central axis of elongated shaft 12 by the same radial distance as satellite lumens 40, 42 are positioned from a central axis of flexible distal tip 30. In some embodiments, satellite lumens 50, 52 may gradually move toward the central axis, starting at any point within transition segment 48. It should be noted that a lumen which extends from one segment of the elongated shaft to another segment of the elongate shaft may be considered a single lumen. For example, satellite lumen 42 of flexible distal tip 30 extends into satellite lumen 52 of transition segment 48, and these two lumens may be considered to be a lumen that extends from the flexible distal tip into the transition segment. Similarly, multiple wires, cables, filaments, etc. may be linked together to form a single pull wire.

Transition element 48 may be immediately proximal to flexible distal tip 30. For purposes herein, regarding shaft segments, the terms "immediately proximal to" or "immediately distal to" mean that no other segments are interposed between two shaft segments. The terms "proximal to" and "distal to", for purposes herein, regarding shaft segments, allow for additional segments to be interposed between two shaft segments.

In one embodiment, transition element 48 is five millimeters in length, but in other embodiments transition element 48 may be any suitable length. For example, transition element 48 may be at least two millimeters, at least three millimeters, at least ten millimeters, or more in length.

FIG. 3C shows the position of pull wire main lumen 54 and pull wires 40, 42 within main shaft 32 of the elongated shaft. It should be noted that multiple pull wire main lumens may be used instead of one pull wire main lumen. The term "pull wire main lumen", for purposes herein, does not require that the lumen be present only with the main shaft of the elongated shaft. The term "pull wire main lumen" describes a lumen that is more central and/or contains more pull wires than a pull wire satellite lumen with which the pull wire main lumen is associated. A pull wire main lumen is often proximal to one or more pull wire satellite lumens. In the case of a satellite lumen extending substantially the entire length of the elongated flexible shaft, i.e., from a bending segment in the flexible distal tip to the catheter handle, the satellite lumen in the proximal region of the shaft would be considered a main lumen.

Figure 3A:
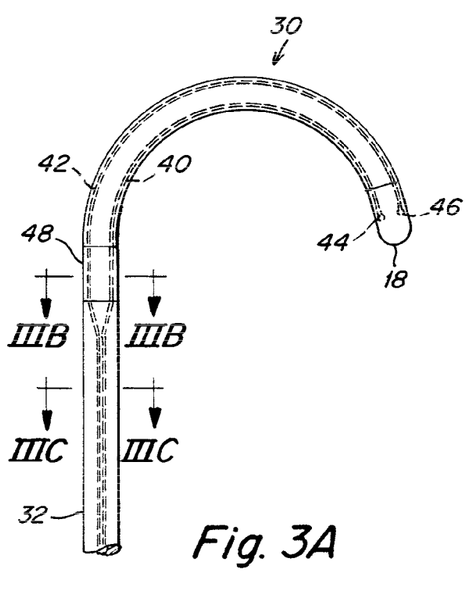
FIG. 3A illustrates one embodiment of the present invention including a pull wire arrangement.
Figure 3B:
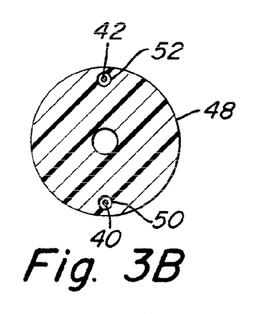
FIG. 3B is a cross-sectional view taken along line IIIB-IIIB of FIG. 3A.
Figure 3C:
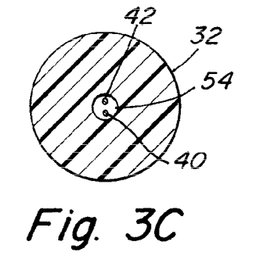
FIG. 3C is a cross-sectional view taken along line IIIC-IIIC of FIG. 3A.

The embodiment illustrated in FIG. 3A includes a transition segment that is located proximal to the change in shaft stiffness. In some embodiments, the transition of the pull wires from satellite lumens to a main lumen may occur distal to a substantial change in shaft stiffness. For example, progressing from a distal tip electrode to a main shaft, an elongated shaft may include: a distal tip electrode; a flexible distal tip segment with a first stiffness and having pull wires in satellite lumens; a transition segment where the pull wires transition to a main lumen, the transition segment having the same (or similar) stiffness as the flexible distal tip; a segment with the pull wires in a main lumen, the segment having the same (or similar) stiffness as the flexible distal tip; and finally a main shaft section having a second stiffness that is greater than the distal segments. In this manner, the transition of the pull wires to the main lumen from the satellite lumens occurs distal to the transition in shaft stiffness, thereby separating the two transitions.

Multiple Bending Segments

To effectively treat a cardiac arrhythmia, a lesion having sufficient dimensions must be created in the heart. Larger lesions are desirable to form an effective conduction block. A relationship has been shown between increased electrode length and increased lesion size, for example due to increased convective cooling of larger electrodes. However, the positioning of the electrode relative to the heart is important to realize the advantages of the increased electrode length. In particular, larger lesions (e.g., in width and length) may result when the electrode used to deliver radiofrequency (RF) energy is positioned parallel, rather than perpendicular, to the endocardial surface. In practice, it can be difficult to position an ablation electrode disposed at the distal tip of a catheter parallel to the endocardial surface. In view of the foregoing, improved methods and apparatuses for configuring a catheter to facilitate placement of the distal tip of the catheter parallel to the endocardial surface will be described.

Figure 4:
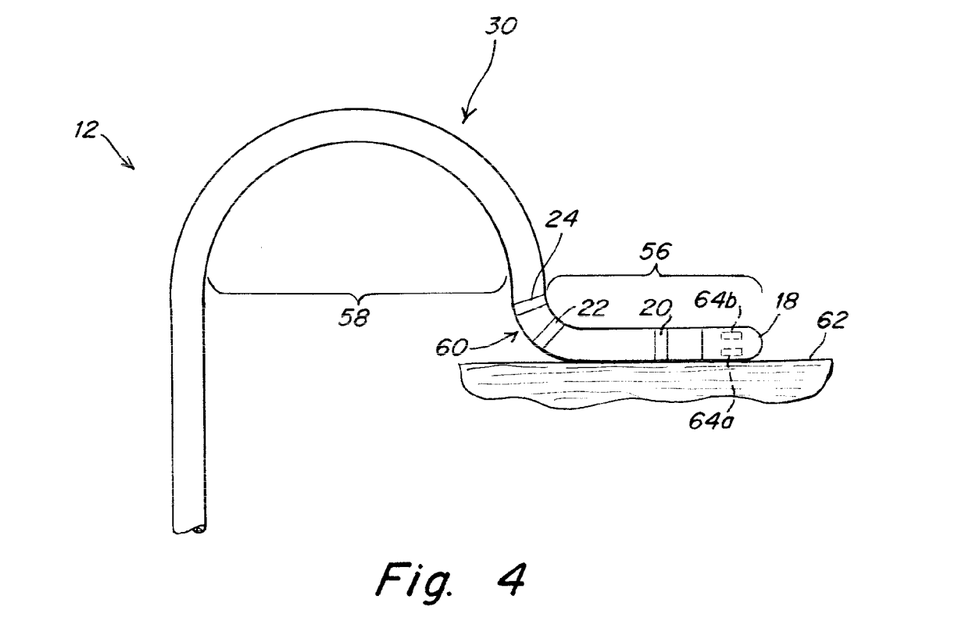
FIG. 4 illustrates one embodiment of a dual-bend catheter with a distal bending segment bent in an opposite direction to a proximal bending segment and contacted to endocardial tissue.

FIG. 4 illustrates an elongated shaft 12 of a catheter having a flexible distal tip 30 which includes a distal bending segment 56 and a proximal bending segment 58. The distal bending segment 56 comprises an ablation electrode 18. According to one embodiment, ablation electrode 18 is approximately four millimeters in length. In other embodiments, ablation electrode 18 may be longer, such as between five millimeters and twelve millimeters, and more particularly, five or eight millimeters. Outer diameters of electrodes and the shaft may be any suitable diameter, and in some embodiments, the electrodes and shaft have a 7 F or 8 F outer diameter. In the illustrated embodiment, distal bending segment 56 also includes a reference electrode 24, and two mapping electrodes 20 and 22, each of which is approximately one millimeter in length. Not all of the illustrated electrodes are required, and one or more additional electrodes, whether ablation, mapping, or pacing, may be added. It should be appreciated that other catheter configurations may have a different electrode configurations within the flexible distal tip of the catheter. For example, the electrode configuration may comprise any combination of one or more ablation, pacing, and/or mapping electrodes. Such electrodes may comprise ring electrodes, tip electrodes, movable electrodes, and/or irregularly shaped electrodes.

Distal bending segment 56 and proximal bending segment 58 may be independently controllable with bending segment manipulation mechanisms. For purposes herein, "independently controllable" or "independently bendable", in relation to two or more bending segments, mean that each bending segment can be bent without substantially affecting the angle of deflection of another bending segment. The bending segment manipulation mechanisms may include any suitable manipulation mechanisms known in the art, for example, the control mechanisms described in U.S. Pat. No. 5,383,852 to Stevens-Wright, U.S. Pat. No. 5,462,527 to Stevens-Wright et al., and U.S. Pat. No. 5,935,102 to Bowden et al., each of which is hereby incorporated by reference herein in its entirety. A bending segment manipulation mechanism for the proximal bending segment may be adapted to deflect the proximal bending segment 58, for example, in a semicircular shape. A bending segment manipulation mechanism for the distal bending segment may be adapted to deflect the distal bending segment 56, for example, to form a bend 60 (e.g., a ninety degree bend).

As discussed above, bend 60 may be formed at a proximal end of the distal bending segment 56. Bend 60 may be a substantially ninety degree bend, and may have a radius of curvature that is smaller than one that may be formed in proximal bending segment 58. Distal bending segment 56 may be bendable in two opposite directions relative to a central axis of the catheter or "bidirectionally bendable." For example, distal bending segment 56 in FIG. 4 is shown to have a bend at an angle that differs by one hundred-eighty degrees relative to the angle of distal bending segment 56 in FIG. 5.

Figure 9:
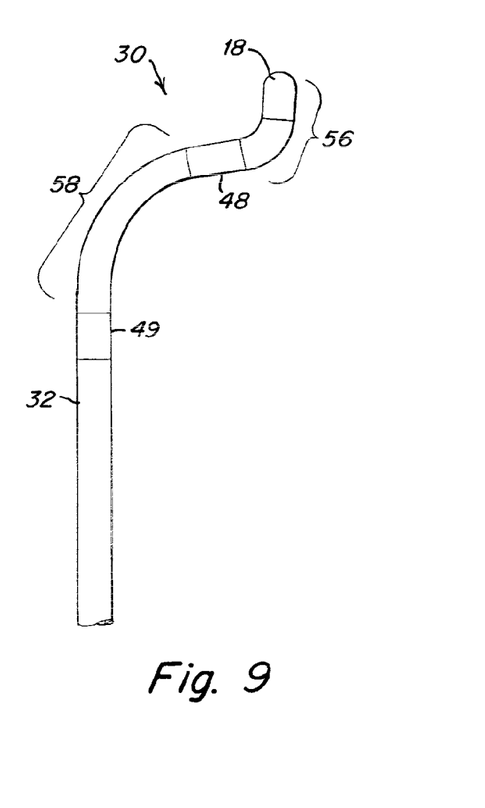
FIG. 9 illustrates another embodiment of a dual-bend catheter having a pull-wire arrangement.

For purposes herein, the term "opposite direction" does not mean a one hundred-eighty degree difference between two directions. The term "opposite direction", specifically in relation to bending shaft segments, means an opposite direction of rotation or sweep of a segment. For example, a distal tip segment bent in a clockwise direction by twenty degrees from a reference axis is considered to be bent in an opposite direction to the distal tip segment being bent thirty degrees in a counterclockwise direction from the reference axis. Further, if a proximal bending segment is bent in a clockwise direction, and a distal bending segment which extends from the proximal bending segment is bent in a counterclockwise direction relative to the distal end of the proximal segment, the distal bending segment is considered to be bent in an opposite direction to the proximal bending segment. An example of such a configuration is illustrated in FIG. 9. It should be appreciated that even though both segments are bent ninety degrees in FIG. 9, the segments may be bent by a lesser or greater amount and still be considered bent in an opposite direction. In some embodiments, a first bending segment may be deflectable in a first plane while a second bending segment is independently deflectable in a second, different, plane.

It should be noted that proximal bending segment 58 and distal bending segment 56 need not be immediately adjacent to one another within a flexible distal tip—a non-bending segment may be interposed between the two bending segments. Also, additional bending segments may be included within flexible distal tip 30 or elsewhere within elongated flexible shaft 12. For example, flexible distal tip 30 may include three, four, or more bending segments. A flexible distal tip need not include only flexible segments. Substantially inflexible segments or components may be included, for example a stiff distal tip electrode, or a stiff plastic shaft segment.

According to one aspect of the invention, distal bending segment 56 is substantially straight distal to bend 60. The stiffness and length of tip electrode 18 may cause distal bending segment 56 to remain substantially straight and/or distal bending segment 56 may be preformed to have a generally straight shape. In some embodiments, pull wires for distal bending segment 56 may be anchored toward the proximal end of distal bending segment 56. According to one embodiment, the distal bending segment is approximately eighteen millimeters in length. In some embodiments, distal bending segment 56 may be any suitable length, such as nineteen millimeters or twenty-two millimeters.

Figure 5:
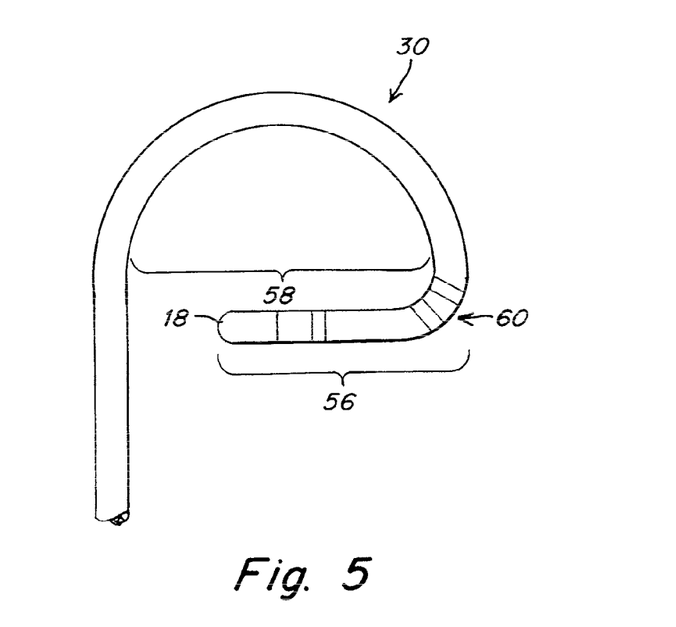
FIG. 5 illustrates the embodiment shown in FIG. 4 with the distal bending segment bent in the same direction as the proximal bending segment.
Figure 6:
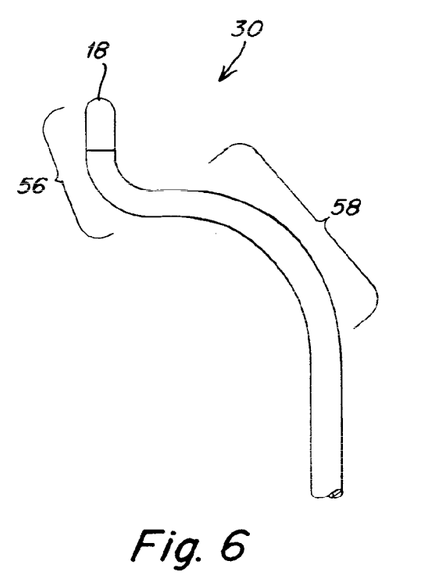
FIG. 6 illustrates another embodiment of a dual-bend catheter with the distal bending segment bent in the opposite direction as the proximal bending segment.
Figure 7:
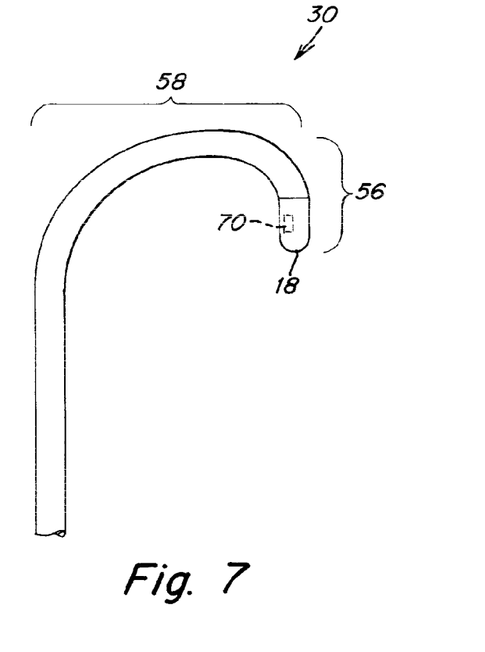
FIG. 7 illustrates another embodiment of a dual-bend catheter with the distal bending segment bent in the same direction as the proximal bending segment.

Proximal bending segment 58 may be controlled to form an arcuate shape. Although the arcuate shape may be formed in any known manner, according to one embodiment, the manipulation mechanism used to control the proximal bending segment section 58 comprises a pull wire anchored near a distal end of the proximal bending segment 58. A pair of pull wires may alternatively be used, for example if bidirectional bending or active straightening of proximal bending segment 58 is desired. FIGS. 4 and 5 show proximal bending segment 58 having a curve that is generally semicircular (i.e., an approximately one hundred-eighty degree arc). FIGS. 6 and 7 show proximal bending segment 58 forming an approximately ninety degree arc.

In FIG. 4, the elongated shaft is configured such that distal bending segment 56 is positioned in a parallel orientation with respect to endocardial tissue 62 and the entire length of distal tip ablation electrode 18 is in contact with endocardial tissue 62. Only one side of ablation electrode 18 is shown contacting tissue 62 in FIG. 4. It may therefore be desirable to include a plurality of thermocouples in electrode 18 positioned so that a thermocouple is located on the tissue side of the ablation electrode for a given tip configuration. In the illustrative embodiment of FIG. 4, a thermocouple 64a may be used when the side of ablation electrode 18 that includes thermocouple 64a is in contact with tissue 62 (e.g., when the catheter is positioned as shown in FIG. 4). Similarly, thermocouple 64b may be used when the side of ablation electrode 18 that includes thermocouple 64b is located is in contact with tissue 62. Wires (not shown), coupled to thermocouples 64a and 64b, transmit signals indicative of a temperature detected by thermocouples 64a and 64b. A switch may be included, for example on a handle of the catheter, to control the activation or transmission of signals from thermocouples 64a and 64b in accordance with the configuration of the flexible distal tip.

FIG. 7 shows a flexible elongated shaft 12 which includes an optional localization sensor 70 that can be used to determine the location of the catheter in a patient. Localization sensor 70 may, for example, be an electromagnetic sensor that is fixed within distal bending segment 56 of flexible tip 30 using any suitable mechanism, such as glue or solder. Localization sensor 70 generates signals indicative of the location of the electromagnetic sensor. A wire (not shown) electrically connects localization sensor 70 to a controller to allow generated signals to be transmitted to the controller for processing.

In addition to the localization sensor 70 fixed within distal bending segment 56 of the flexible distal tip, a second localization sensor (not shown) may optionally be provided that is fixed relative to the patient. The second localization sensor may be attached, for example, to the patient's body, and serves as a reference sensor. A magnetic field is also provided, which is exposed to the localization sensors. Coils within each localization sensor generate electrical currents when exposed to the magnetic field. The electrical current generated by the coils of each sensor corresponds to a position of each sensor within the magnetic field. Signals generated by the reference localization sensor and localization sensor 70 are analyzed by the controller to ascertain a precise location of localization sensor 70. Further details of performing localization using electromagnetic sensors are provided in U.S. Pat. No. 5,694,945, which is hereby incorporated by reference in its entirety.

As an alternative to the use of electromagnetic sensors other conventional techniques, such as ultrasound or magnetic resonance imaging (MRI) can also be used for localization of the catheter. Details of performing localization using ultrasound are provided in U.S. Pat. Nos. 6,212,027 and 5,820,568, which are hereby incorporated by reference in their entireties. Moreover, an impedance-based sensor can also be incorporated into the catheter. In an impedance-based system, several, such as three, high frequency signals are generated along different axes. The catheter electrodes may be used to sense these frequencies, and with appropriate filtering, the strength of the signal and thus the position of the catheter can be determined. Details of an impedance based system are provided in U.S. Pat. No. 5,983,126, which is hereby incorporated by reference in its entirety. One skilled in the art will appreciate that the construction of catheters of the various types described herein may be optimized to make use of the various localization techniques.

Transition Segment in Combination with Dual-Bend Catheter

Figure 8:
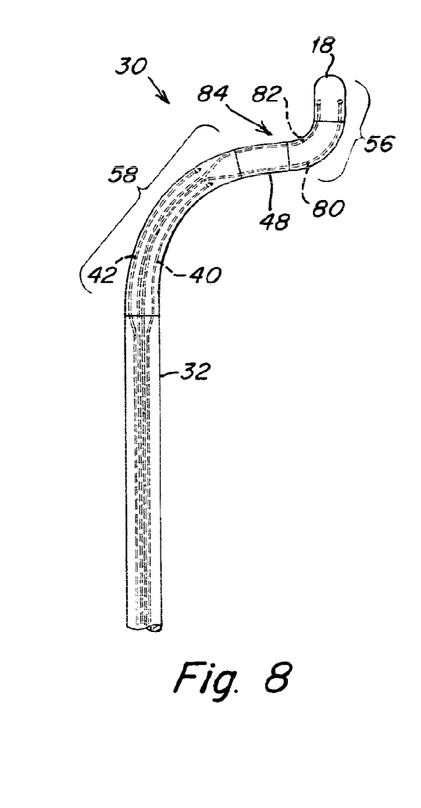
FIG. 8 illustrates one embodiment of a dual-bend catheter having a pull-wire arrangement.

Transition segment 48, as described above with reference to FIGS. 3A-3C, may be implemented in combination with a flexible distal tip having two independently controllable bending segments. As illustrated in FIG. 8, transition segment 48 is positioned between distal bending segment 56 and proximal bending segment 58. As described above, transition segment 48 can be helpful in improving the reliability and ease of deflecting a bending segment. This advantage may be more noticeable when transition element is positioned between two bending segments. By separating the transition of distal bending segment pull wires 80, 82 from a location 84 of a transition of segment stiffness, stresses on pull wires 80, 82 may be reduced.

FIG. 9 illustrates a dual-bend flexible distal tip 30 which includes two transition segments 48 and 49. The pull wire lumens and pull wires may be arranged in a similar manner to the arrangements described above with reference to FIG. 8, but may include an additional transition segment 49 positioned proximally to proximal bending segment 58.

Flat Wire in Combination with Multiple Bending Segments

When bending different segments of a flexible distal tip, it may be desirable to maintain the segments within the same plane. When one segment is bent in an opposite direction to another segment, the segments may tend to twist, thereby taking the segments out of a common plane. Additionally, a bidirectionally bendable segment also may tend to twist or change bending planes. To help maintain the segments within the same plane, one or more flat wires may be included within the flexible distal tip.

Figure 11:
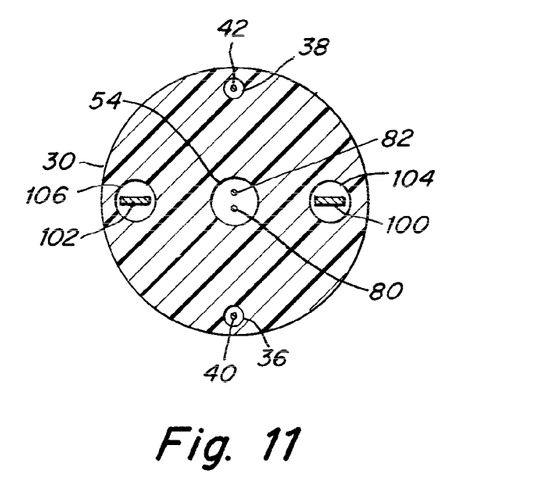
FIG. 11 is a cross-sectional view taken along line XI-XI of FIG. 10.

A cross-sectional view of one type of flat wire is illustrated in FIG. 11 where rectangular flat wires 100 and 102, due to their geometry, tend to resist bending in the horizontal directions (as viewed in FIG. 11) and allow bending in the vertical directions of a flexible distal tip 30. In some embodiments, other flat wire geometries may be used to perform the same function. In some embodiments, a composite material or other orthotropic material may be used to form a stiffening wire that acts similarly to a flat-shaped wire without having a flat cross-section. For purposes herein, a stiffening wire that provides a bending stiffness in a first direction within an axial cross-sectional plane that is greater than a stiffness provided in a second direction within the same axial cross-sectional plane is considered to be a flat wire. While rectangular flat wires are used in some embodiments, flat wires of any suitable size and shape may be used.

Flat wires 100, 102 reside within flat wire lumens 104, 106, which may be positioned at locations offset by ninety degrees from pull wire lumens 36, 38. Proximal bending segment pull wires 40, 42 are shown in lumens 36, 38 and distal bending segment pull wires 80, 82 are shown in pull wire main lumen 54. Flat wires 100, 102 may extend partially or completely through flexible distal tip 30. In one embodiment, the flat wires extend from a proximal end of proximal bending segment 58 to a location distal to a longitudinal anchor location for the proximal bending segment pull wires (the longitudinal anchor location for the proximal segment pull wires may be near to a the transition of proximal bending segment 58 to distal bending segment 56). In some embodiments, the flat wires may extend into distal bending segment 56 on the distal end, and/or may extend into main shaft 32 on the proximal end. In some embodiments, the flat wires may reside only in distal bending segment 56. One or more axially-slidable flat wires may be implemented such that a user may establish the longitudinal position(s) of the flat wire(s).

Flat wire 100, 102 are formed of 304 stainless steel in some embodiments, but any suitable material may be used, for example, nitinol or other shaped memory alloys. Instead of exactly two flat wires, as shown in the embodiment illustrated in FIG. 11, one flat wire, or three or more flat wires may be used. In embodiments including multiple flat wires, each flat wire does not necessarily have to extend along the same length of flexible elongated shaft 12, nor does each flat necessarily have to have the same geometry or stiffness.

Figure 10:
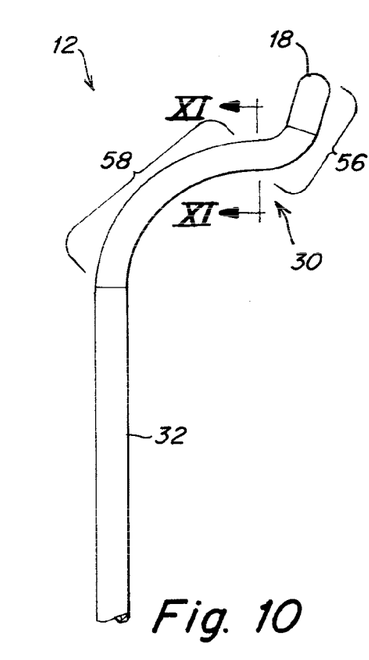
FIG. 10 illustrates an embodiment of a dual-bend catheter that includes two flat wires.

The plane in which the two or more bending segments bend, relative to the main shaft, may be determined by securing flat wires 100, 102 in a certain rotational orientation. For example, in the embodiment shown in FIGS. 10 and 11, the orientation of flat wires 100, 102 can be secured such that proximal bending segment 58 and distal bending segment 56, shown in FIG. 10, bend only within the plane of the page.

Floating Flat Wire

In some conventional catheters, when flat wires are used within flexible shafts, each flat wire is sized to fit closely within its flat wire lumen. If a flat wire becomes twisted, such an arrangement may lead to the flat wire remaining twisted due to friction with the lumen walls. In embodiments of the present invention, one or more flat wires are allowed to "float" within a lumen. In such embodiments, the flat wire lumen is sized to have a dimension that is slightly smaller than the lumen such that the flat wire is free to rotate about its longitudinal axis within the lumen. Upon initial bending of the segment in which the flat wire resides, the flat wire orients itself such that the shaft may continue to bend in the same direction. After a certain amount of bending, the flat wire engages the lumen and the flat wire is not longer free to rotate. Once engaged, the flat wire may serve as a stiffening member and/or torque transmitter.

Figure 12:
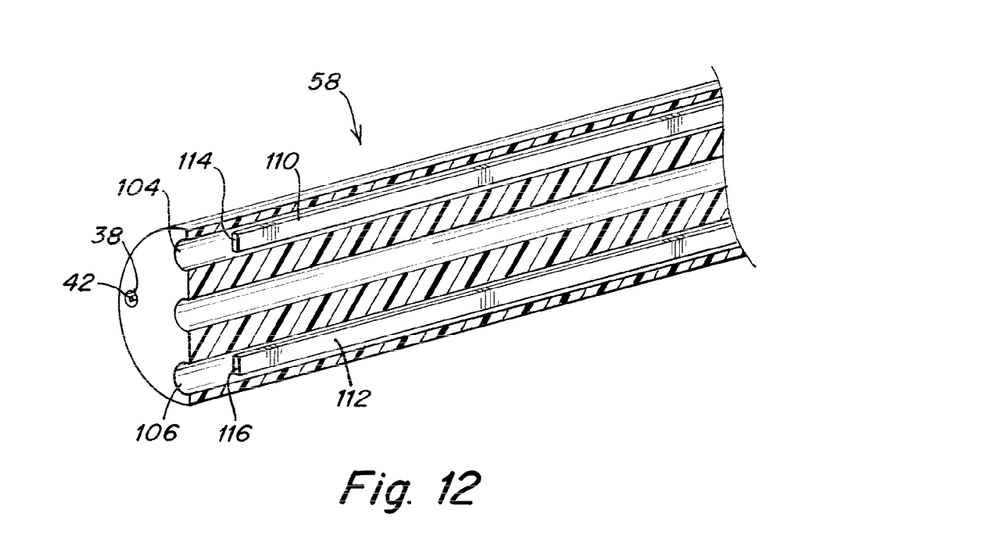
FIG. 12 is a perspective view of longitudinal cross-section a catheter that includes flat wires with at least one free end.

FIG. 12 shows a longitudinal cross-section of a portion of a proximal bending segment 58 according to one embodiment of the invention, including two flat wires 110 and 112 which are free to rotate upon initial bending of bending segment 58.

Flat wires 110, 112 may extend partially or completely through flexible distal tip 30. In one embodiment, the flat wires extend from a proximal end of proximal bending segment 58 to a location distal to an anchor point for the proximal bending segment pull wires. The distal ends of flat wires 110, 112 may extend into a distal bending segment, and/or the proximal ends of flat wires 110, 112 may extend into a main shaft. In some embodiments, the flat wires may reside only in a distal bending segment.

As can be seen in FIG. 12, flat wires 110, 112 are not as wide as lumens 104, 106, and distal ends 114, 116 of flat wires 110, 112 are not secured to bending segment 58. In such an arrangement, flat wires 104, 106 may be rotated when bending segment 58 is bent in various directions. For example, if bending segment 58 is bent downwardly (as viewed in FIG. 12), flat wires 104, 106 may rotate ninety degrees such that their wider widths are oriented horizontally. Once bending segment 58 is sufficiently bent, flat wires 104, 106 engage with the walls of lumens 104, 106 and are no longer free to rotate. In an engaged state, flat wires 104, 106 may increase the bending and/or torsional stiffness of bending segment 58.

It should be appreciated that one, two, three, four, or more flat wires may be used within a bending segment. Additionally, one or more flat wires within a bending segment may be unsecured, while others may be secured.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A catheter comprising:
   an elongated flexible shaft including:
   a distal bending segment;
   a proximal bending segment;
   a main shaft that is proximal to the proximal bending segment;
   an activation element main lumen extending along at least a portion of the proximal bending segment and the main shaft;
   a first activation element satellite lumen which extends along at least a portion of the distal bending segment; and a second activation element satellite lumen which extends along at least a portion of the proximal bending segment;
a first activation element anchored at a first anchoring point and extending proximally from the first anchoring point, through at least a portion of the distal bending segment within the first satellite lumen, through the proximal bending segment and into the main shaft; and
a second activation element anchored at a second anchoring point and extending proximally from the second anchoring point, through at least a portion of the proximal bending segment within the second satellite lumen, and into the main shaft; wherein:
the first satellite lumen starts a transition to the main lumen distal to the second anchoring point.

2. A catheter as in claim 1, wherein the main lumen is closer to a center axis of the catheter shaft than the first satellite lumen.

3. A catheter as in claim 2, wherein the main lumen is positioned on the center axis of the catheter shaft.

4. A catheter as in claim 1, wherein the first activation element comprises a first activation wire.

5. A catheter as in claim 4, wherein the first activation wire comprises a first pull wire.

6. A catheter as in claim 5, wherein the second activation element comprises a second pull wire.

7. A catheter as in claim 6, wherein actuation of the first pull wire bends the distal bending segment in a direction that is different from a direction that actuation of the second pull wire bends the proximal bending segment.

8. A catheter as in claim 7, wherein actuation of the first pull wire and the second pull wire bends the distal bending segment and the proximal bending segment within substantially the same plane.

9. A catheter as in claim 1, further comprising:
a third activation element satellite lumen which extends along at least a portion of the distal bending segment;
a fourth activation element satellite lumen which extends along at least a portion of the proximal bending segment;
a third activation element anchored at a third anchoring point and extending proximally from the third anchoring point, through at least a portion of the distal bending segment within the third satellite lumen, through the proximal bending segment and into the main shaft; and
a fourth activation element anchored at a fourth anchoring point and extending proximally from the fourth anchoring point, through at least a portion of the proximal bending segment within the fourth satellite lumen, and into the main shaft; wherein
the third satellite lumen starts a transition to the main lumen distal to the fourth anchoring point.

10. A catheter as in claim 9, wherein:
the third activation element comprises a third pull wire, the fourth activation element comprises a fourth pull wire;
actuation of the third pull wire bends the distal bending segment in a direction that is different from a direction that actuation of the fourth pull wire bends the proximal bending segment; and
actuation of the third pull wire and the fourth pull wire bends the distal bending segment and the proximal bending segment within substantially the same plane.

11. A catheter as in claim 10, wherein actuation of the first pull wire and the fourth pull wire bends the distal bending segment and the proximal bending segment within substantially the same plane.

12. A catheter as in claim 1, further comprising a transition segment between the distal bending segment and the proximal bending segment, wherein the first satellite lumen extends from the distal bending segment into the transition segment, and transitions to the main lumen in the transition segment.

13. A catheter as in claim 12, wherein the transition segment has a stiffness that is greater than a stiffness of the distal bending segment.

14. A catheter comprising:
an elongated flexible shaft including:
a distal bending segment;
a proximal bending segment;
a main shaft that is proximal to the proximal bending segment;
a first pull wire satellite lumen which extends along at least a portion of the distal bending segment; and
a second pull wire satellite lumen which extends along at least a portion of the proximal bending segment;
a first pull wire anchored at a first anchoring point in the distal bending segment and extending proximally from the first anchoring point, through at least a portion of the distal bending segment within the first satellite lumen, through the proximal bending segment and into the main shaft; and
a second pull wire anchored at a second anchoring point and extending proximally from the second anchoring point, through at least a portion of the proximal bending segment within the second satellite lumen, and into the main shaft; wherein:
the first satellite lumen starts a transition toward a center axis of the catheter at a position which is distal to the second anchoring point.

15. A catheter as in claim 14, further comprising a main pull wire lumen positioned at or near the center axis of the catheter shaft, wherein the first pull wire extends through the main pull wire lumen within the proximal bending segment.

16. A catheter as in claim 15, further comprising a transition segment where the first pull wire transitions to the main lumen, the transition segment being located between the distal bending segment and the proximal bending segment.

17. A catheter as in claim 16, wherein the transition segment has a stiffness that is greater than a stiffness of the distal bending segment.

18. A catheter as in claim 14, wherein:
actuation of the first pull wire bends the distal bending segment in a direction that is different from a direction that actuation of the second pull wire bends the proximal bending segment; and
actuation of the first pull wire and the second pull wire bends the distal bending segment and the proximal bending segment within substantially the same plane.

19. A catheter as in claim 14, further comprising:
a third pull wire satellite lumen which extends along at least a portion of the distal bending segment;
a fourth pull wire satellite lumen which extends along at least a portion of the proximal bending segment;
a third pull wire anchored at a third anchoring point in the distal bending segment and extending proximally from the third anchoring point, through at least a portion of the distal bending segment within the third satellite lumen, through the proximal bending segment and into the main shaft; and
a fourth pull wire anchored at a fourth anchoring point and extending proximally from the fourth anchoring point, through at least a portion of the proximal bending segment within the fourth satellite lumen, and into the main shaft; wherein the third satellite lumen starts a transition to the main lumen distal to the fourth anchoring point.

20. A catheter as in claim 19, wherein:
actuation of the third pull wire bends the distal bending segment in a direction that is different from a direction that actuation of the fourth pull wire bends the proximal bending segment; and
actuation of the first pull wire and the fourth pull wire bends the distal bending segment and the proximal bending segment within substantially the same plane.

* * * * *